(12) United States Patent
Majka et al.

(10) Patent No.: US 11,739,295 B2
(45) Date of Patent: Aug. 29, 2023

(54) METHOD OF OBTAINING PIGMENTED CELLS IN VITRO BY THE DIFFERENTIATION OF HUMAN INDUCED PLURIPOTENT STEM CELLS

(71) Applicant: UNIWERSYTET JAGIELLOŃSKI, Cracow (PL)

(72) Inventors: Marcin Majka, Wieliczka (PL); Maciej Sułkowski, Cracow (PL)

(73) Assignee: UNIWERSYTET JAGIELLONSKI, Cracow (PL)

(*) Notice: Subject to any disclaimer, the term of this patent is extended or adjusted under 35 U.S.C. 154(b) by 275 days.

(21) Appl. No.: 16/649,041

(22) PCT Filed: Sep. 21, 2018

(86) PCT No.: PCT/PL2018/050049
§ 371 (c)(1),
(2) Date: Mar. 19, 2020

(87) PCT Pub. No.: WO2019/059792
PCT Pub. Date: Mar. 28, 2019

(65) Prior Publication Data
US 2020/0216804 A1  Jul. 9, 2020

(30) Foreign Application Priority Data
Sep. 21, 2017  (PL) .......................... 422916

(51) Int. Cl.
*C12N 5/071* (2010.01)
(52) U.S. Cl.
CPC ........ *C12N 5/0626* (2013.01); *C12N 2506/45* (2013.01)
(58) Field of Classification Search
None
See application file for complete search history.

(56) References Cited

U.S. PATENT DOCUMENTS

| | | | | |
|---|---|---|---|---|
| 5,380,359 A | * | 1/1995 | Honda | A61K 8/0241 |
| | | | | 106/482 |
| 2013/0183674 A1 | * | 7/2013 | Studer | A61P 25/02 |
| | | | | 435/7.1 |
| 2016/0213717 A1 | * | 7/2016 | Xu | A61K 35/36 |

FOREIGN PATENT DOCUMENTS

JP  2015146803 A  8/2015

OTHER PUBLICATIONS

Fang et al., Stem Cells 2006; 24: 1668-1677 (Year: 2006).*
Mull et al., Int. J. Mol. Sci. 2015, 16, 30458-30469 (Year: 2015).*
Stepień et al., J Am Soc Mass Spectrom 2009, 20, 464-468 (Year: 2009).*
Shao et al., Journal of Molecular Cell Biology (2015), 7(5), 441-454 (Year: 2015).*
Callahan, S. J. et al., "Feeder-free Derivation of Melanocytes from Human Pluripotent Stem Cells", Journal of Visualized Experiments, Mar. 2016, 109, e53806, 1-6, doi: 10.3791/53806.
Nissan, X. et al., "Functional melanocytes derived from human pluripotent stem cells engraft into pluristratified epidermis", Proceedings of the National Academy of Sciences, Sep. 2011, vol. 108, No. 36, 14861-14866, Epub Aug. 19, 2011, doi: 10.1073/pnas.1019070108.
Ohta, S. et al., "Generation of Human Melanocytes from Induced Pluripotent Stem Cells" Plos One, Jan. 2011, vol. 6, issue 1, e16182, doi: 10.1371/journal.pone.0016182.
Efthymiou, A. G. et al., "Self-renewal and cell lineage differentiation strategies in human embryonic stem cells and induced pluripotent stem cells", Expert Opinion on Biological Therapy, Sep. 2014, 14(9): 1333-1344, Epub May 2014, doi: 10.1517/14712598.2014.922533.
International Search Report and Written Opinion, PCT/PL2018/050049, dated Jan. 23, 2019.

* cited by examiner

*Primary Examiner* — Evelyn Y Pyla
(74) *Attorney, Agent, or Firm* — Arrigo, Lee, Guttman & Mouta-Bellum LLP

(57) ABSTRACT

The invention discloses the method of differentiating human induced Pluripotent Stem cells (iPS cells) to obtain pigmented cells which produce melanin. The protocol described is much more efficient than any other method used to obtain melanin in vitro.

7 Claims, 5 Drawing Sheets

A

B

Figure 1:
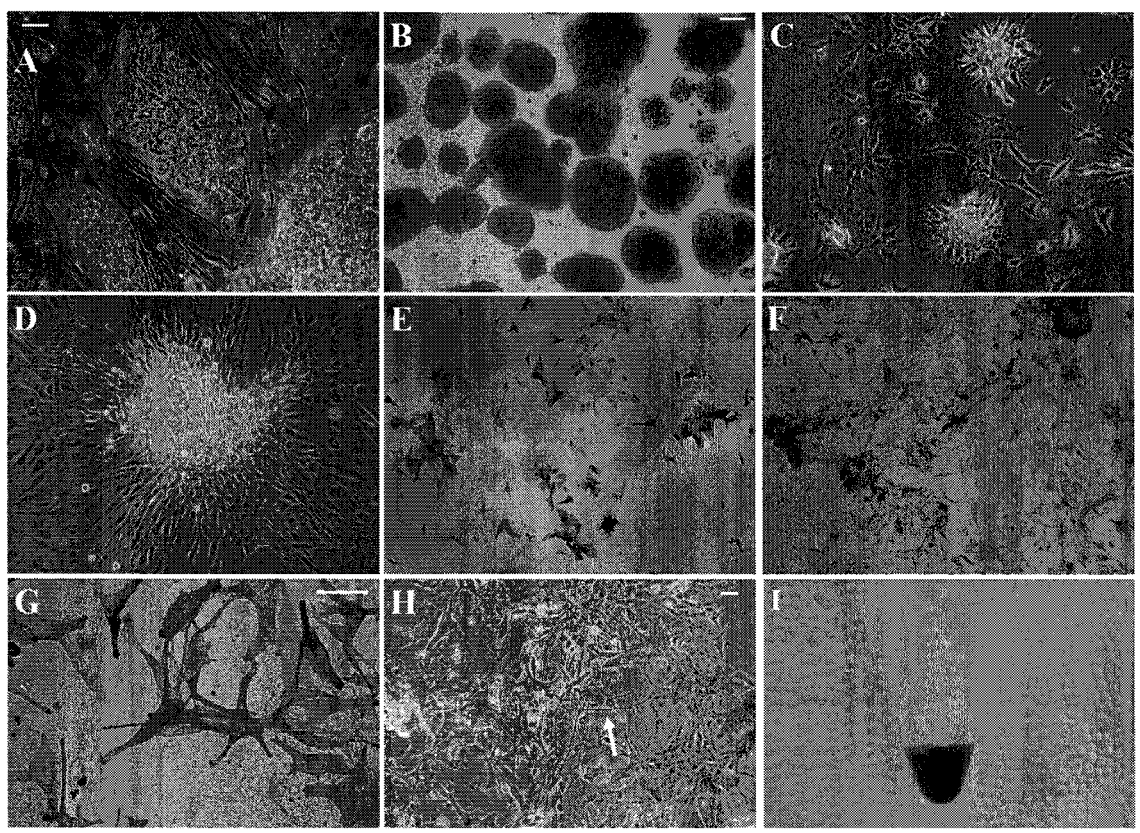

METHOD OF OBTAINING PIGMENTED CELLS IN VITRO BY THE DIFFERENTIATION OF HUMAN INDUCED PLURIPOTENT STEM CELLS

The invention is the method of differentiating human induced pluripotent stem cells (iPS cells) to obtain pigmented cells. The cells obtained using this protocol produce a black pigment—melanin.

Melanin is a natural skin pigment whose sources so far have been very limited. Melanin is isolated from skin or hair biopsies, but the amounts thus obtained are very small and in a highly degraded form. The methods of obtaining pigmented cells in vitro which have been used so far are extremely ineffective.

The aim of the invention is to provide an effective way of obtaining human cells rich in melanin.

Unexpectedly, the above-mentioned aim was achieved in this invention.

The subject of the invention is the method of obtaining pigmented cells in vitro by the differentiation of human induced pluripotent stem cells, which involves three steps:
a) the suspension of detached confluent iPS cells is plated on a non-adherent cell culture dish in the medium for iPS cells without bFGF with inhibitor Y27632 where the density is $2\text{-}2.5\times10^4$ cells/cm$^2$ and then cultured for 4 days until embryoid bodies (EB) are formed,
b) the embryoid bodies obtained in step a) are harvested and seeded on an adherent dish and then cultured in the medium for iMEF cells for 18 hours,
c) progenitors are selected in medium N1 consisting of supplement N2, (diluted 1×), fibronectin in the concentration of 250 ng/ml, the solution of antibiotics containing penicillin and streptomycin (P/S) in the concentration of 100 U/ml/100 µg/ml, diluted in medium DMEM/F12, the progenitors are selected for 10 days and dead cells are periodically eliminated while the medium components are periodically replenished,
d) the obtained progenitor cells are dissociated and seeded in the density of $0.5\text{-}2\times10^5$/cm$^2$ on dishes covered with laminin and polyornithine where they expand for 7 days in medium N2 consisting of supplement N2, (diluted 1×), laminin in the concentration of 1 mg/ml, bFGF in the concentration of 20 µg/ml, FGF8 in the concentration of 100 ng/ml and P/S in the concentration of 100 U/ml/100 µg/ml, diluted in medium DMEM/F12. The obtained cells may be stored frozen in medium N2 with 10% of DMSO in the density of 2 million cells/ml before they are used in the next step,
e) for 7-16 days the cells are terminally differentiated by culturing them in medium N3 consisting of supplement N2, (diluted 1×), laminin in the concentration of 1 mg/ml, dibutyryl-cAMP in the proportion of 0.5 nM, ascorbic acid in the concentration of 200 µM and P/S in the concentration of 100 U/ml/100 µg/ml, diluted in medium DMEM/F12, until human cells pigmented with melanin are obtained.

Media N1, N2 and N3 contain the indicated ingredients only.

The next subject of the invention is the application of the cells obtained using the method indicated in the invention described above to obtain melanin.

The cell culture grown in vitro in accordance with the invention makes a convenient and, at the same time, unlimited source of melanin available in a non-degraded form. The methods of obtaining melanin in vitro known so far do not have the efficiency comparable to the invention. The invention makes it possible to obtain significant amounts of the pigment ready for biophysical tests in a short time and at a relatively low cost. Isolated melanin may have many industrial applications, including that of a substrate for the development of a new generation of natural UV protection lotions. The cells obtained may also be used as a natural substitute of melanocytes in the treatment of patients with vitiligo. The protocol of obtaining pigmented cells can be found below.

EXAMPLE 1

The Method of Obtaining Human Cells Extensively Pigmented with Melanin From Human Induced Pluripotent Stem Cells The cells used were confluent piPS cells (protein-iPS cells) purchased from System Bioscience (cat no.SC801A-1, SC802A-1) (Kim et al. 2009) or the cell lines derived at the Department of Transplantation of the Jagiellonian University Medical College by reprogramming the somatic cells from donors.

In the first step, the confluent iPS cells (FIG. 1A) cultured on the feeder layer made of iMEF cells were harvested using Accutase and plated as a suspension of single cells on a non-adherent cell culture dish in the medium for iPS cells without bFGF with inhibitor Y27632 in the density of $2\text{-}2.5\times10^4$/cm$^2$. Next, iPS cells were cultured in the suspension for 4 days until embryoid cells (EB) were formed (FIG. 1B).

The composition of the medium for iPS cells:

| Component | Concentration |
| --- | --- |
| KSR (ThermoFisher Scientific) | 20% |
| β-Mercaptoethanol (Sigma-Aldrich) | 0.1 mM |
| Non-essential Amino Acids (ThermoFisher Scientific) | 1× |
| Penicillin/Streptomycin (P/S) (ThermoFisher Scientific) | 100 U/ml/100 µg/ml |
| bFGF (ThermoFisher Scientific) | 10 ng/ml |
| DMEM/F12 (ThermoFisher Scientific) | |

In the next step, the embryoid cells were harvested, centrifuged (300 rpm, 5 minutes) and seeded on an adherent dish with the same surface as the non-adherent dish in the medium for iMEF cells.

The composition of the medium for iMEF cells:

| Component | Concentration |
| --- | --- |
| Foetal Bovine Serum (EurX) | 10% |
| L-glutamine (ThermoFisher Scientific) | 2 mM |
| P/S | 100 U/ml/100 µg/ml |
| DMEM 4.5 g/l (Lonza) | |

After about 18 hours, the selection of progenitors (FIG. 1C) was initiated by changing the medium to medium N1 with the following composition:

| Component | Concentration |
| --- | --- |
| Supplement N2 (ThermoFisher Scientific) | 1× |
| Fibronectin (ThermoFisher Scientific) | 250 ng/ml |
| P/S | 100 U/ml/100 µg/ml |
| DMEM/F12 (ThermoFisher Scientific) | |

The selection in serum-free media was carried out for 10 days by removing dead cells and providing the fresh medium N1 every second day. Supplement N2 provided by Life Technologies was used. It contains human insulin (0.1 mg/ml), holo-Transferrin (5 µg/ml), progesterone (20 µM), putrescine (0.1 mM), sodium selenite (30 nM) (final concentration, after dilution in the medium).

The next step was the expansion of selected progenitors (FIG. 1D). The cells were dissociated into single cells using trypsin and plated in the density of $0.5\text{-}2\times10^5/cm^2$ onto dishes covered with laminin and poly-ornithine.

Cell expansion was carried out for 7 days in medium N2 with the following composition:

| Component | Concentration |
| --- | --- |
| N2 supplement | 1× |
| Laminin (ThermoFisher Scientific) | 1 mg/ml |
| bFGF | 20 µg/ml |
| FGF8 (ThermoFisher Scientific) | 100 ng/ml |
| P/S | 100 U/ml/100 µg/ml |
| DMEM/F12 | |

Progenitors were frozen in medium N2 with 10% of DMSO in the density of $2\times10^6$ cells/ml. After the expansion was completed, the cells were terminally differentiated by changing the medium from N2 to N3. The composition of medium N3 can be found in the table below:

| Component | Concentration |
| --- | --- |
| N2 supplement | 1× |
| Laminin | 1 mg/ml |
| Dibutyryl cAMP (Sigma-Aldrich) | 0.5 mM |
| Ascorbic acid (Sigma-Aldrich) | 200 µM |
| P/S | 100 U/ml/100 µg/ml |
| DMEM/F12 | |

As a result of the differentiation method described extensively pigmented cells (FIG. 1E-I) were obtained in a highly repeatable manner. The efficiency of the differentiation process was always similar and made it possible to obtain a large number ($>3\times10^6$) of highly pigmented cells.

FIG. 1 presents the results of the consecutive stages of iPS cell differentiation to obtain pigmented cells. A—piPS cells cultured on the feeder layer. B—multi-cellular embryoid bodies (EB) in a suspension. C—selected NPC cells subjected to expansion (D). In the final stage of differentiation, the cells acquired a black pigmentation (E-I).

EXAMPLE 2

The Characteristics of the Cells Obtained and the Pigment Isolated From Them

Figure 2:
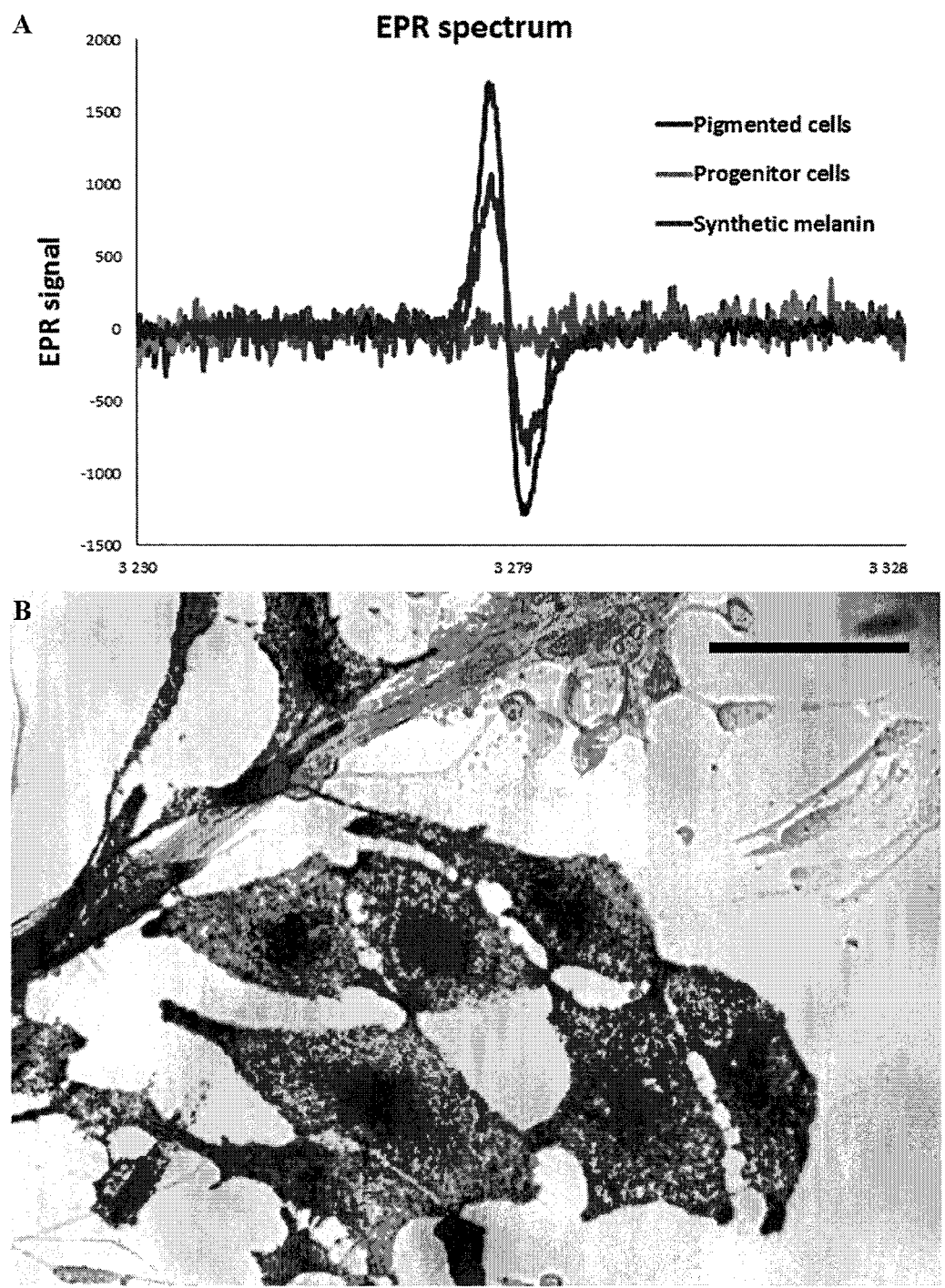

The pigment obtained was unambiguously identified as melanin using electron paramagnetic resonance (EPR) (FIG. 2A) and Fontana-Masson staining (FIG. 2B). The obtained pigmented cells were characterised with respect to their gene expression using a RT-PCR reaction (FIG. 3) and immunocytochemical staining (ICC) (FIG. 4).

Figure 3:
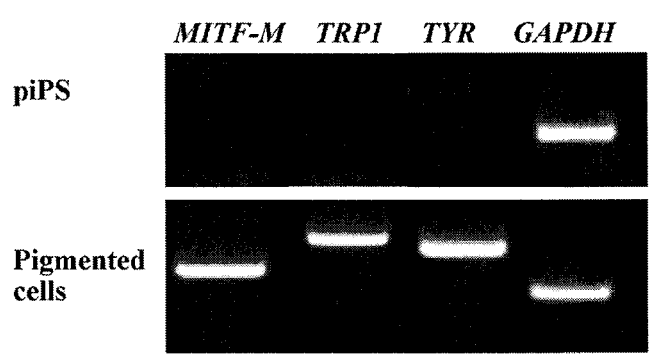
Figure 3:
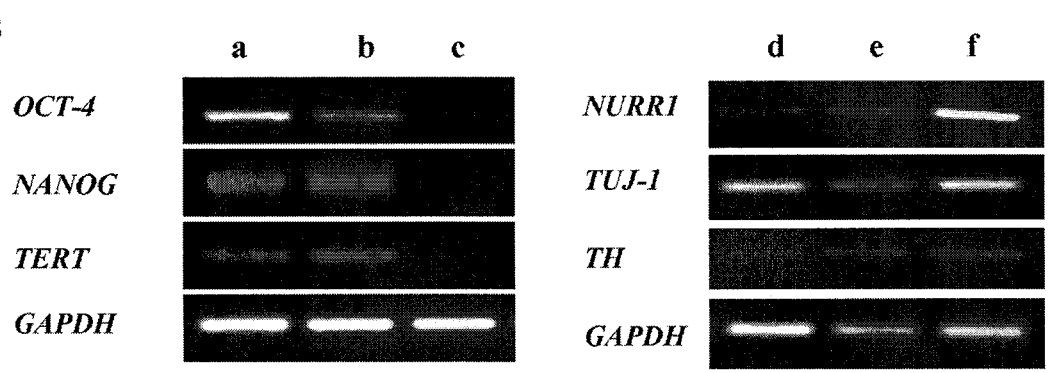

FIG. 3 shows the expression of markers at the RNA level. A—pigmented cells which, unlike iPS cells, express melanocyte markers (MITF-M, TRP1, TYR) B—in the next steps of cell differentiation (A-F) the expression of embryoid markers is reduced (OCT-4, NANOG, TERT) and the expression of neuroectodermal markers (NURR1, TUJ-1, TH) grows. TERT—telomerase, TUJ-1—βIII-tubulin, TH—tyrosine hydroxylase NURR1—nuclear-receptor related protein, the constitutive gene GAPDH was used as a positive control of the PCR reaction.

Figure 4:
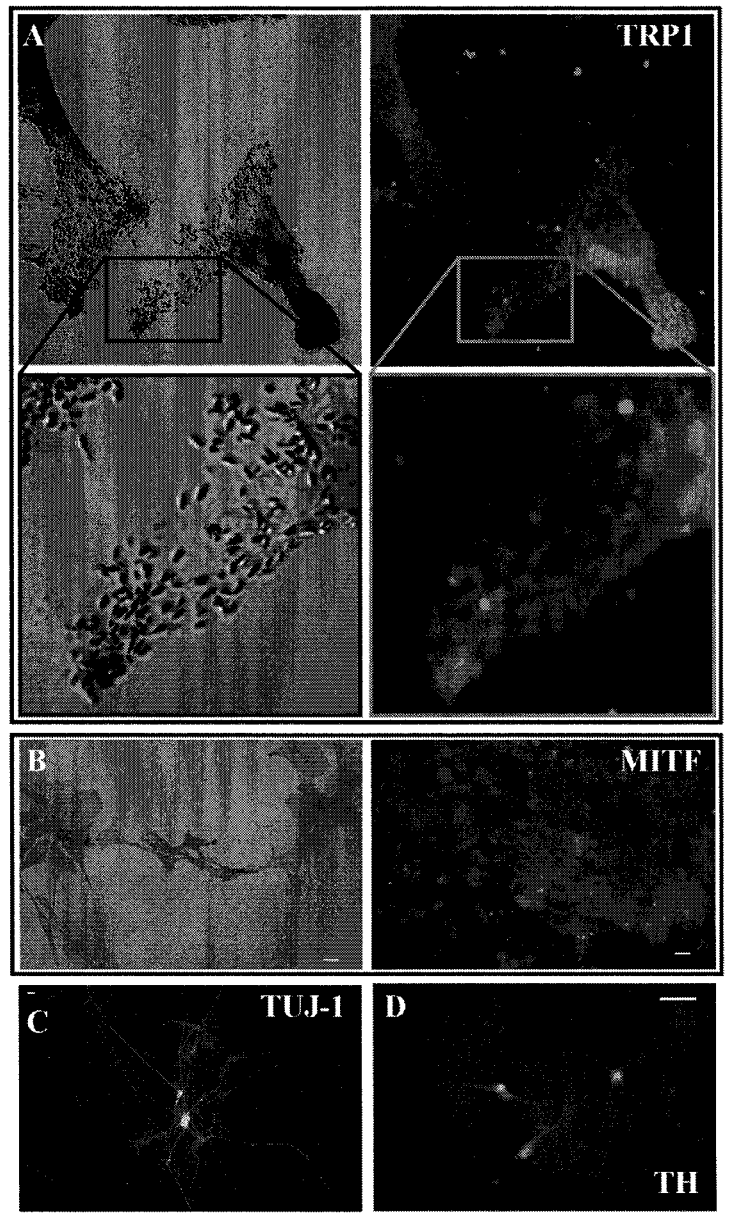

FIG. 4 shows the expression of markers at the level of protein. The cells obtained express melanocyte markers—TRP1 and MITF (A and B). In the heterogenic population of cells obtained, there are also dopaminergic neurons which express TUJ-1 and TH (C and D). The subcellular location of melanin was defined using transmission electron microscopy (TEM) (FIG. 5).

Figure 5:
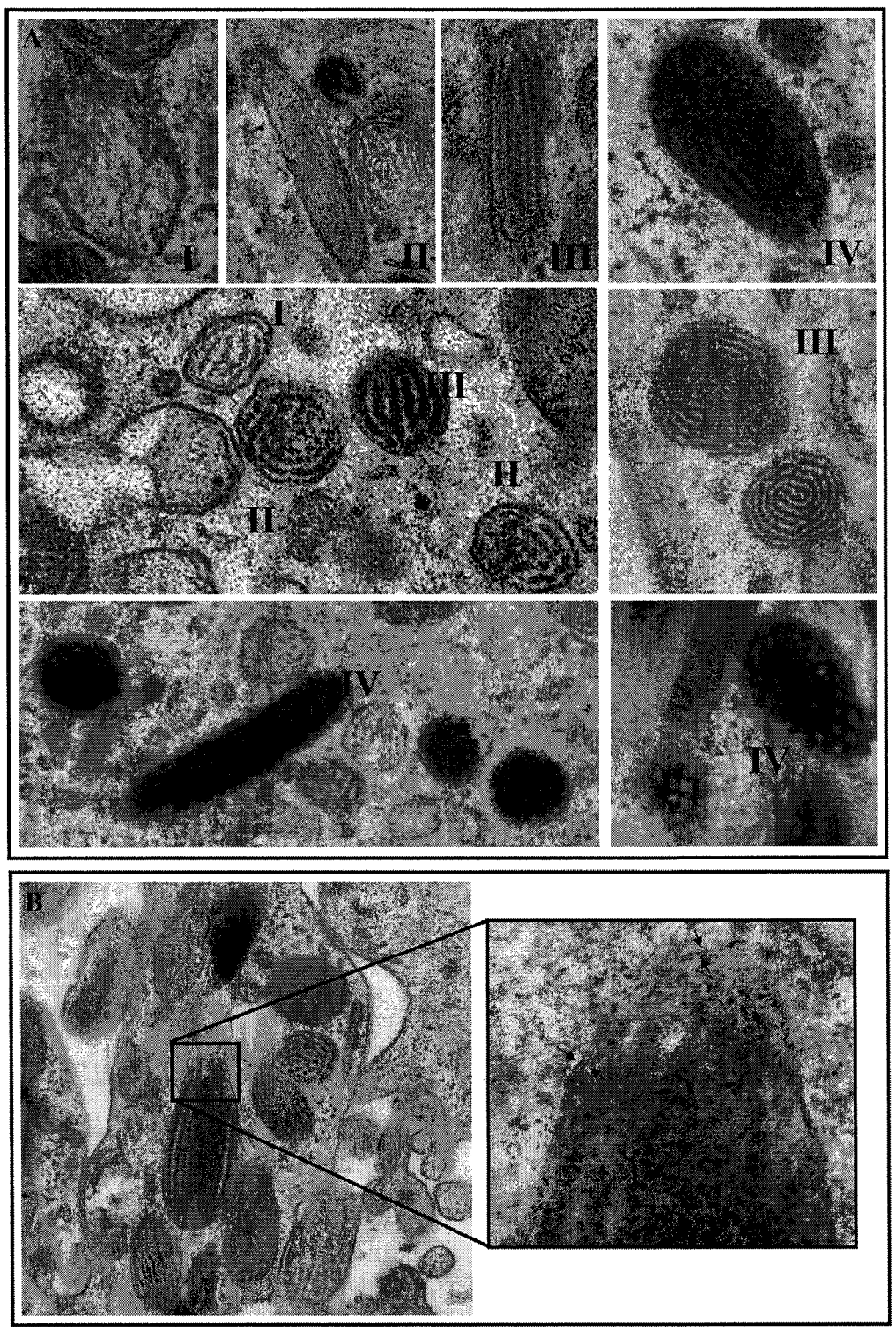

FIG. 5 shows the subcellular location of melanin in the cells obtained. Melanin is organised in organelles resembling the consecutive stages of melanosome development (I-IV in A). The organelles are surrounded with a dual cellular membrane (B).

The results obtained make it possible to confirm unambiguously that the pigment obtained is melanin. The differentiated pigmented cells resemble melanocytes in many aspects (marker expression, gene expression profile, the presence of membranous intracellular organelles filled with the pigment), but the number of pigmented cells and the level of pigmentation for the cells obtained is unexpectedly high as compared with other available technologies. The method described can be employed to provide very large numbers of extensively pigmented cells that may be used for the isolation of pure, non-degraded melanin in large amounts and at a relatively low cost.

The invention claimed is:

1. The method of obtaining pigmented cells in vitro by differentiating human induced pluripotent stem (iPS) cells, comprising:
    a) plating a suspension of detached confluent iPS cells on a non-adherent cell culture dish in iPS cell medium that does not comprise bFGF and does comprise inhibitor Y27632, where the density is $2\text{-}2.5\times10^4$ cells/cm² and culturing to form embryoid bodies (EB),
    b) harvesting and seeding the embryoid bodies on an adherent cell culture dish and then culturing in iMEF culture media for at least 18 hours to generate progenitor cells,
    c) selecting the progenitor cells for 10 days with periodic removal of dead cells in medium N1 comprising supplement N2 at 1× concentration fibronectin in the concentration of 250 ng/ml, a solution of antibiotics including penicillin and streptomycin (P/S) in the concentration of 100 U/ml penicillin / 100 µg/ml streptomycin, diluted in medium DMEM/F12,
    d) dissociating the progenitor cells and placing the progenitor cells at a density of $0.5\text{-}2\times10^5/cm^2$ onto dishes covered with laminin and polyornithine, and expanding the progenitor cells for 7 days in medium N2 comprising supplement N2 at 1× concentration, laminin in the concentration of 1 mg/ml, bFGF in the concentration 20 µg/ml, FGF8 in the concentration of 100 ng/ml and P/S in the concentration of 100 U/ml penicillin / 100 µg/ml streptomycin, diluted in medium DMEM/F12, and e) differentiating the expanded progenitor cells for 7-16 days by culturing them in medium N3 comprising supplement N2 at 1× concentration, laminin in the concentration of 1 mg/ml, dibutyryl-cAMP in the concentration of 0.5 mM, ascorbic acid in the concentration of 200 µM and P/S in the concentration of 100 U/ml penicillin / 100 µg/ml streptomycin, diluted in medium DMEM/F12, in order to obtain human cells pigmented with melanin.

2. The method according to the claim 1 characterized in that media N1, N2 and N3 contain the indicated components only.

3. The method of claim 2, further comprising isolating the melanin from the cells.

4. The method of claim 1, further comprising isolating the melanin from the cells.

5. The method of claim 4, further comprising administering the melanin to a patient.

6. The method of claim 4, further comprising making a cream comprising the melanin.

7. The method of claim 1, further comprising administering the cells obtained according to the method to a patient.

* * * * *